US009322822B2

(12) United States Patent
Kuroda et al.

(10) Patent No.: US 9,322,822 B2
(45) Date of Patent: Apr. 26, 2016

(54) METHOD FOR DETECTING ASBESTOS

(75) Inventors: Akio Kuroda, Hiroshima (JP); Takenori Ishida, Hiroshima (JP); Tomoki Nishimura, Hiroshima (JP)

(73) Assignee: Hiroshima University, Hiroshima (JP)

(*) Notice: Subject to any disclaimer, the term of this patent is extended or adjusted under 35 U.S.C. 154(b) by 0 days.

(21) Appl. No.: 14/238,137

(22) PCT Filed: Aug. 9, 2012

(86) PCT No.: PCT/JP2012/070783
§ 371 (c)(1),
(2), (4) Date: Feb. 10, 2014

(87) PCT Pub. No.: WO2013/024881
PCT Pub. Date: Feb. 21, 2013

(65) Prior Publication Data
US 2014/0170773 A1 Jun. 19, 2014

(30) Foreign Application Priority Data
Aug. 12, 2011 (JP) .................... 2011-177254

(51) Int. Cl.
C07K 1/13 (2006.01)
G01N 33/53 (2006.01)
G01N 21/64 (2006.01)

(52) U.S. Cl.
CPC ........ *G01N 33/5308* (2013.01); *G01N 21/6428* (2013.01); *G01N 21/6458* (2013.01)

(58) Field of Classification Search
CPC .......... G01N 33/5308; G01N 2500/02; G01N 21/6428; G01N 21/6458; G01N 2333/47; C07K 1/13
See application file for complete search history.

(56) References Cited

U.S. PATENT DOCUMENTS

| 5,635,363 A * | 6/1997 | Altman et al. ............... 435/7.24 |
| 2009/0098578 A1 | 4/2009 | Kuroda et al. |
| 2009/0118142 A1 | 5/2009 | Kuroda et al. |

FOREIGN PATENT DOCUMENTS

| JP | 2010-32271 A | 2/2010 |
| JP | 2010-85248 A | 4/2010 |
| JP | 2010-256010 A | 11/2010 |
| WO | WO9928344 | * 11/1998 |
| WO | 2007/055243 A1 | 5/2007 |

OTHER PUBLICATIONS

Ishida et al. (Environ Sci Technol, 2010. 44,755-759).*
Mammen et al (Angew. Chem. Int. Ed. 1998, 37, 2754-2794).*
Asbestos Monitoring Manual, Air Environment Division, Environmental Management Bureau, the Ministry of of the Environment of Japan, Fourth Edition, Jun. 2010, (2 pages of Partial English Translation and 28 pages of Official Copy).
"Asbestos Monitoring Manual (Fourth Edition)", The Air Environment Division, Environmental Management Bureau, the Ministry of the Environment of Japan, Jun. 2010, 91 pages (8 pages of Partial Translation and 83 pages of Official Copy).
Kuroda et al., "Detection of Chrysotile Asbestos by Using a Chrysotile-Binding Protein", Biotechnology and Bioengineering, vol. 99, No. 2, Feb. 1, 2008, pp. 285-289.
International Preliminary Report on Patentability received for PCT Patent Application No. PCT/JP2012/070783, mailed on Feb. 20, 2014, 20 pages (10 pages of English Translation and 10 pages of Official Copy).
International Search Report and Written Opinion received for PCT Patent Application No. PCT/JP2012/070783, mailed on Sep. 25, 2012, 8 pages (1 page of English Translation of ISR and 7 pages of Official Copy).
Office Action received for Chinese Patent Application No. 201280039165.9, mailed on Mar. 30, 2015, 18 pages (9 pages of English Translation and 9 pages of Official Copy).
"Determination of Dust in the Air of Workplace Part 5: Asbestos Fiber Concentration, Issued by Ministry of Health of the PRC", National Occupational Hygiene Standards of the People's Republic of China, GBZ/T 192.5-2007, Jun. 18, 2007, 18 pages (8 pages of English Translation and 10 pages of Official Copy).

* cited by examiner

*Primary Examiner* — Shafiqul Haq
*Assistant Examiner* — Carmencita M Belei
(74) *Attorney, Agent, or Firm* — Morrison & Foerster LLP

(57) ABSTRACT

In order to provide a method for more efficiently, easily, and accurately detecting asbestos without changing the asbestos detection criterion of the phase-contrast microscope/electron microscope method as compared with the phase-contrast microscope/electron microscope method, a phase-contrast microscope and a fluorescence microscope are used in combination to detect asbestos contained in a test sample after the test sample is made contact with an asbestos-binding protein having a fluorescent label.

5 Claims, 3 Drawing Sheets

SEQUENCE LISTING

<160> NUMBER OF SEQ ID NOS: 8

<210> SEQ ID NO 1
<211> LENGTH: 49
<212> TYPE: DNA
<213> ORGANISM: Artificial Sequence
<220> FEATURE:
<223> OTHER INFORMATION: Synthesized Oligonucleotide

<400> SEQUENCE: 1
gctcagaaaa tcgaatggca cgaacaccac caccaccacc actgaacta         49

<210> SEQ ID NO 2
<211> LENGTH: 51
<212> TYPE: DNA
<213> ORGANISM: Artificial Sequence
<220> FEATURE:
<223> OTHER INFORMATION: Synthesized Oligonucleotide

<400> SEQUENCE: 2
ctcgaagatg tcgttcagac cgccaccctc gagtgcggcc gcaagcttgt c       51

<210> SEQ ID NO 3
<211> LENGTH: 27
<212> TYPE: DNA
<213> ORGANISM: Artificial Sequence
<220> FEATURE:
<223> OTHER INFORMATION: Synthesized Oligonucleotide

<400> SEQUENCE: 3
catatgcaat atcgcgaaat gctgatc                                  27

<210> SEQ ID NO 4
<211> LENGTH: 29
<212> TYPE: DNA
<213> ORGANISM: Artificial Sequence
<220> FEATURE:
<223> OTHER INFORMATION: Synthesized Oligonucleotide

<400> SEQUENCE: 4
ggatccaaac aacgtttagc tttggtgcc                                29

<210> SEQ ID NO 5
<211> LENGTH: 33
<212> TYPE: DNA
<213> ORGANISM: Artificial Sequence
<220> FEATURE:
<223> OTHER INFORMATION: Synthesized Oligonucleotide

<400> SEQUENCE: 5
ggaattcgct agcatgcaag aagggcaaaa ccg                           33

<210> SEQ ID NO 6
<211> LENGTH: 34
<212> TYPE: DNA
<213> ORGANISM: Artificial Sequence
<220> FEATURE:
<223> OTHER INFORMATION: Synthesized Oligonucleotide

<400> SEQUENCE: 6
gttggatccc cgcagccagc catctgtttt tcgc                          34

<210> SEQ ID NO 7
<211> LENGTH: 57
<212> TYPE: PRT
<213> ORGANISM: Escherichia coli str. K-12 substr. MG1655

```
<400> SEQUENCE: 7

Met Ser Glu Ala Leu Lys Ile Leu Asn Asn Ile Arg Thr Leu Arg Ala
 1               5                  10                  15

Gln Ala Arg Glu Cys Thr Leu Glu Thr Leu Glu Glu Met Leu Glu Lys
            20                  25                  30

Leu Glu Val Val Asn Glu Arg Arg Glu Glu Glu Ser Ala Ala Ala
         35                  40                  45

Ala Glu Val Glu Glu Arg Thr Arg Lys
     50                  55

<210> SEQ ID NO 8
<211> LENGTH: 31
<212> TYPE: PRT
<213> ORGANISM: Escherichia coli str. K-12 substr. MG1655

<400> SEQUENCE: 8

Gln Tyr Arg Glu Met Leu Ile Ala Asp Gly Ile Asp Pro Asn Glu Leu
 1               5                  10                  15

Leu Asn Ser Leu Ala Ala Val Lys Ser Gly Thr Lys Ala Lys Arg
             20                  25                  30
```

METHOD FOR DETECTING ASBESTOS

CROSS REFERENCE TO RELATED APPLICATIONS

This is a U.S. National Phase patent application of PCT/JP2012/070783, filed on Aug. 9, 2012, which claims priority to Japanese Patent Application No. 2011-177254, filed on Aug. 12, 2011, each of which is hereby incorporated by reference in the present disclosure in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 247322019800SEQLIST.txt, date recorded: Feb. 6, 2014, size: 3 KB).

TECHNICAL FIELD

The present invention relates to a method for detecting asbestos.

BACKGROUND ART

In recent years, adverse influences of asbestos (fibrous silicate, also called Ishiwata in Japanese) on human bodies have become a problem. Specifically, companies announced that many people engaged in production of asbestos or in businesses handling asbestos in the past were suffering from health hazards such as lung cancer or mesothelioma. It was also reported that persons who inhaled asbestos dust have a risk of health problems such as pulmonary asbestosis, lung cancer, and malignant mesothelioma.

Pulmonary asbestosis is one kind of pulmonary fibrosis (pneumoconiosis) which is a disease making lungs fibrous. Although there are many causes, such as other mineral dust, for such fibrous lungs, pulmonary fibrosis caused by exposure to asbestos is especially referred to as pulmonary asbestosis, thereby being distinguished from the others. It is believed that asbestos fibers cause lung cancer mainly by physical stimulus caused by asbestos fibers taken in lung alveoli. The degree of carcinogenicity is varied among different kinds of asbestos, while diameter and length of asbestos also affect how carcinogenic the asbestos is. Malignant mesothelioma is a malignant tumor developed, for example, in pleura surrounding lungs and in peritoneum surrounding organs such as liver and stomach.

Asbestos encompasses chrysotile (white asbestos), crocidolite (blue asbestos), amosite (brown asbestos), anthophylite, toremolite, and actinolite. As for usage of asbestos, 90 percent or more is for building materials, and remaining 10 percent is industrial materials such as sealing materials for chemical plant facilities, friction materials, and the like. Although production etc. of building materials, friction materials, and adhesives made of asbestos has been prohibited since Oct. 1, 2004, there still remains asbestos in many buildings because asbestos had been used in large amounts in the past.

One example of a method for detecting asbestos is as follows. In detection of asbestos in an atmosphere, the atmosphere is sucked by a pump through a filter for collecting asbestos, and the filter is made colorless (transparent) with the use of acetone or the like and is then observed with the use of a phase-contrast microscope to measure a total fiber concentration in the atmosphere. In a case where the total fiber concentration is 1 or more fibers/L, it is determined with the use of an electron microscope whether fibers found by the observation by the phase-contrast microscope are actually asbestos or not (see Non-Patent Literature 1).

However, since observation using a phase-contrast microscope requires good skill and a considerable length of time, it is difficult to simultaneously carry out many observation processes. Moreover, since an electron microscope is a very expensive machine, it is not easy for everyone to conduct electron microscopic observation. Furthermore, determination using an electron microscope requires not only complicated sample pretreatment etc., but also a lot of time and patience because fibers observed by a phase-contrast microscope need be analyzed by an energy dispersive X-ray analyzer.

For these reasons, the conventional method using a phase-contrast microscope and an electron microscope (hereinafter referred to as "phase-contrast microscope/electron microscope method") cannot speedily detect asbestos, and is therefore inapt for detecting an asbestos risk at a demolition work site where speedy detection is required. At a demolition work site, demolition is finished within two or three days at the earliest. Therefore, there are quite a few cases where asbestos has been already scattered around before an inspection result is obtained. Since asbestos generation sources in Japan are shifting from factories to demolition work sites, whose location change in a short time, there is an urgent need to develop a method for speedily detecting asbestos.

By the way, the inventors of the present invention independently discovered a protein which specifically binds to asbestos (referred to as "asbestos-binding protein"), and advocates an asbestos bioassay system using this protein (referred to as "bio-fluorescence method") (see, for example, Patent Literature 1). The bio-fluorescence method is a method for detecting asbestos under a fluorescence microscope with the use of a bioprobe prepared by modifying the asbestos-binding protein with a fluorescent substance. The bio-fluorescence method makes it possible to detect, with good sensitivity, even finer asbestos fibers which are hard to observe under a phase-contrast microscope. Specifically, it is found that the bio-fluorescence method makes it possible to detect even fine chrysotile single fiber whose width (diameter) is 30 nanometers. Moreover, the bio-fluorescence method makes it possible to find out both physical properties and shapes of asbestos fibers. For these reasons, the bio-fluorescence method has been attracting attention as an efficient, easy and accurate asbestos detecting method.

Moreover, the inventors of the present invention reported that a DksA protein derived from *Escherichia coli* strongly binds to especially chrysotile (white asbestos) among a variety of asbestos (Non-Patent Literature 2).

Furthermore, the inventors of the present invention disclosed a screening method for an asbestos-binding protein and a method for detecting asbestos contained in a variety of samples by the bio-fluorescence method with the use of an asbestos-binding protein obtained by the screening method (Patent Literature 2).

CITATION LIST

Patent Literature 1
WO2007-055243 (Publication Date: May 18, 2007)
Patent Literature 2
Japanese Patent Application Publication, Tokukai, No. 2010-32271 A (Publication Date: Feb. 12, 2010)

Non-Patent Literature 1
"Asbestos Monitoring Manual (Fourth Edition)", the Air environment Division, Environmental Management Bureau, the Ministry of the Environment of Japan, June, 2010

Non-Patent Literature 2
"Detection of Chrysotile Asbestos by Using a Chrysotile-Binding Protein", Biotechnology and Bioengineering, Vol. 99, No. 2, Feb. 1, 2008, p. 285-289.

SUMMARY OF INVENTION

Technical Problem

As described above, the bio-fluorescence method makes it possible to detect even fine asbestos fibers which cannot be detected by a phase-contrast microscope. This, however, may lead to such a risk that the total number of asbestos detected by the bio-fluorescence method exceeds the total number of asbestos detected by a phase-contrast microscope. This arouses, among persons who have been measuring asbestos with the use of the conventional art, concerns such as "Is there continuity with past data obtained by the conventional phase-contrast microscope/electron microscope method?" and "There may arise a need to change a criterion for asbestos detection". Therefore, a technical challenge of the bio-fluorescence method is to develop how to measure asbestos while not changing the conventional criterion of the phase-contrast microscope/electron microscope method.

According to Non-Patent Literature 1, the criterion of the conventional method is as follows. First, a phase-contrast microscope is used to measure fibrosis substances having a length of 5 μm or more, a width (diameter) of less than 3 μm, and a length-width ratio (aspect ratio) of 3:1 or more and to calculate the total number of fibers. Then, percentage of asbestos to the total number of fibers is determined by some kind of method. One example of such an asbestos determining (identifying) method using an electron microscope (scanning electron microscope for analysis or a transmission electron microscope for analysis) is the phase-contrast microscope/electron microscope method. According to this method, an electron microscope is used to determine, on the basis of X-ray spectra, asbestos in the fibers measured by a phase-contrast microscope.

Meanwhile, the phase-contrast microscope/electron microscope method has a problem that it cannot detect asbestos easily and speedily, as described above.

The present invention was accomplished in view of the above problems, and an object of the present invention is to provide a method which makes it possible to detect asbestos more efficiently, easily and accurately as compared with the phase-contrast microscope/electron microscope method without changing the asbestos detection criterion of the phase-contrast microscope/electron microscope method.

Solution to Problem

As a result of diligent studies for attaining the above object, the inventors of the present invention found that by (i) narrowing substances to be detected down under a phase-contrast microscope according to the conventional criterion and then (ii) checking physical properties of these substances by the bio-fluorescence method, asbestos can be detected more efficiently, easily and accurately as compared with the phase-contrast microscope/electron microscope method without changing the asbestos detection criterion of the phase-contrast microscope/electron microscope method. Based on this finding, the inventors of the present invention accomplished the present invention.

Such an idea of detecting asbestos by (i) narrowing substances to be detected down under a phase-contrast microscope according to the detection criterion of the phase-contrast microscope/electron microscope method and then (ii) determining physical properties of these substances (i.e., whether they are asbestos or not) by the bio-fluorescence method is previously unheard of, and is disclosed herein for the first time by the inventors of the present invention.

Specifically, a method according to the present invention for detecting asbestos includes: the contact step of bringing an asbestos-binding protein having a fluorescent label into contact with a test sample; the first detection step of detecting, after the contact step, a fibrous substance contained in the test sample with use of a phase-contrast microscope; and the second detection step of detecting, with use of a fluorescence microscope, the asbestos-binding protein that has bound to the fibrous substance detected in the first detection step, the first detection step and the second detection step being carried out with an identical visual field.

According to the method of present invention for detecting asbestos, first, in the first detection step, a fibrous substance contained in a test sample is detected under a phase-contrast microscope, and then, in the subsequent second detection step using the bio-fluorescence method, it is determined whether each fibrous substance detected in the first detection step is asbestos or not. Although fine asbestos fibers that cannot be detected by a phase-contrast microscope are naturally observed in the second detection step, such fine asbestos fibers are excluded in the first detection step. That is, there is no such a risk that the total number of asbestos finally detected by the method of present invention for detecting asbestos exceeds the total number of asbestos detected in a case where the same sample is examined by the phase-contrast microscope. It is therefore possible to detect asbestos without changing the asbestos detection criterion of the phase-contrast microscope/electron microscope method. In this manner, the method of present invention for detecting asbestos combines a phase-contrast microscope and a fluorescence microscope to detect asbestos.

Moreover, in the first detection step, a physical property of a detection object (i.e., whether it is asbestos or not) that has been narrowed down under the phase-contrast microscope is determined by the bio-fluorescence method in the second detection step. That is, whether or not an asbestos-binding protein having a fluorescent label binds to the detection object is determined on the basis of presence or absence of fluorescence. It is therefore possible to very easily and accurately detect asbestos.

Furthermore, it is possible to easily determine a physical property of a detection object within an extremely short period of time as compared with a case where the physical property is determined according to the conventional electron microscope method. Specifically, according to the electron microscope method, it takes about 15 hours to determine a physical property of a detection object (including a period of time for pretreatment of a sample) (see, for example, Mari YAMADA et al. "Kankyotyu No Ishiwata Hunjin Noudo Sokutei Ni Okeru Bunseki Houhou No Kento", Annual Report of Tochigi Prefectural Institute of Public Health and Environmental Science, No. 12 (2006), page 62-68). Meanwhile, according to the method of present invention for detecting asbestos, it is possible to complete all the steps from the contact step to the second detection step within approximately 1 hour.

According to the phase-contrast microscope/electron microscope method, whether or not asbestos is contained in a test sample can be confirmed by an electron microscope, but observation in an identical visual field is very difficult because this method involves movement of a stage between two kinds of microscopes. That is, it is almost impossible to determine, for each fiber, which of the fibers detected under the phase-contrast microscope is asbestos. This necessitates estimating the number of asbestos by finding the statistically significant number of asbestos with the use of the electron microscope and multiplying the percentage of the asbestos thus found with the total number of fibers found by the phase-contrast microscope.

On the other hand, according to the method of present invention for detecting asbestos, use of a microscope (phase-contrast/fluorescence microscope) including a capacitor for a phase-contrast microscope and an epifluorescence device or a polarized light microscope including these two makes it possible to carry out the first detection step and the second detection step without changing a visual field just by switching a light path from transmitting light for phase-contrast observation to epifluorescence. It is therefore possible to carry out the second detection step in an identical visual field by narrowing down a detection object with the use of a phase-contrast microscope in the first detection step and then just switching a light path of the microscope from a phase-contrast mode to a fluorescence mode. This makes it possible to instantly determine whether each of the fibrous substances detected in the first detection step is asbestos or not.

According to the method of present invention for detecting asbestos, it is therefore possible to more efficiently, easily, and accurately detect asbestos as compared with the phase-contrast microscope/electron microscope method without changing the asbestos detection criterion of the phase-contrast microscope/electron microscope method.

Note that the technique of Non-Patent Literature 2 is a technique of merely confirming that fluorescence emitted by GFP is observed on a chrysotile (white asbestos) fiber on the basis of a phase-contrast microscope image and a fluorescence microscope image of the chrysotile after the chrysotile is made contact with a GFP-labeled DksA protein. That is, observation using the phase-contrast microscope and observation using the fluorescence microscope are carried out just to confirm that the DksA protein is surely bound to chrysotile (white asbestos).

Similarly, although Patent Literature 2 describes that both of observation using a phase-contrast microscope and observation using a fluorescence microscope are carried out, Patent Literature 2 merely describes this fact.

According to the method described in Non-Patent Literature 2 and the method described in Patent Literature 2, both of observation using a phase-contrast microscope and observation using a fluorescence microscope are carried out, but the asbestos detection criterion is the same as that of the conventional bio-fluorescence method. That is, according to the method described in Non-Patent Literature 2 and the method described in Patent Literature 2, substances on which fluorescence was observed are all judged asbestos. It is therefore impossible to accurately detect asbestos by applying the conventional detection criterion.

Patent Literature 2 describes that in a case where asbestos to which a fluorescently-labeled asbestos-binding protein is bound is observed on a filter, the filter is made colorless (transparent). This is simply to make it possible to carry out both of observation using the phase-contrast microscope and observation using the fluorescence microscope. For the reason described above, just by making the filter transparent, it is impossible to accurately detect asbestos by applying the conventional detection criterion.

Specifically, in Examples (e.g., Example 3) of Patent Literature 2, an asbestos-binding protein that has bound to asbestos is identified on the basis of both of observation using the phase-contrast microscope and observation using the fluorescence microscope. However, according to the above technique, fibers that should be picked up in observation using a phase-contrast microscope (specifically, fibers having a predetermined size) are not selected out. This causes all of fluorescent signals observed by the fluorescence microscope (all of the fluorescent signals from large ones to small ones) to be counted as asbestos. As a result, a judgment result obtained by the above technique is largely deviated from that based on the conventional asbestos detection criterion.

In Examples (e.g., Examples 4, 5, 7, 8, 9, and 10) of Patent Literature 2, asbestos and an asbestos-binding protein are caused to bind to each other in a state where they are dispersed in a solution, and enzyme activity of a label linked to the asbestos-binding protein is detected in the state where they are dispersed in the solution. That is, the above technique is not a technique of identifying asbestos on the basis of observation using a phase-contrast microscope and observation using a fluorescence microscope.

In Examples (e.g., Example 6) of Patent Literature 2, asbestos is trapped in a membrane filter, and an asbestos-binding protein is caused to bind to the asbestos, and then the membrane filter is made transparent (see, for example, Example 6 of Patent Literature 2). Then, asbestos is identified on the basis of both of observation using a phase-contrast microscope and observation using a fluorescence microscope. However, this technique has the same problem as the technique of Example 3 described above. Specifically, fibers that should be picked up (specifically, fibers having a predetermined size) in the observation using a phase-contrast microscope are not selected out, and therefore all of fluorescent signals observed by the fluorescence microscope (all of the fluorescent signals from large ones to small ones) are counted as asbestos. As a result, a judgment result obtained by the above technique is largely deviated from that based on the conventional asbestos detection criterion.

As described above, the judgment results obtained by the techniques described in Examples etc. of Patent Literature 2 are largely deviated from that based on the conventional asbestos detection criterion. This is described below in more detail.

Even a very thin fiber (e.g., a chrysotile fiber having a diameter of 30 nm) can be detected by a fluorescence microscope. Specifically, even a very thin fiber can be observed since, under a fluorescence microscope, an object to be observed looks luminous against a dark field. Since a fluorescence microscope is just one kind of optical microscope, there is a limit (250 nm to 300 nm) in optical resolution. Even so, a fluorescence microscope allows even a fiber of 30 nm for example to be observed as a thick blurred one larger in size (approximately 300 nm) than an actual size.

That is, since fibers that are equal to or smaller than the optical resolution limit can be observed by a fluorescence microscope, there is a high risk that more fibers are counted than a case where a phase-contrast microscope is used. Moreover, a measured value around the optical resolution limit has a risk of including a value lower than the measured value, and is therefore unreliable.

The method of present invention for detecting asbestos provides a method for solving the above problems.

Specifically, according to the present invention, fibers that meet the conventional asbestos size condition are first detected by a phase-contrast microscope, and then only the fibers that meet this condition are examined on the basis of a fluorescent image as to whether they are asbestos or not. It is thus possible to solve the above problems.

Advantageous Effects of Invention

According to the method of present invention for detecting asbestos, it is possible to produce an effect of detecting asbestos more efficiently, easily and accurately as compared with the phase-contrast microscope/electron microscope method without changing the asbestos detection criterion of the phase-contrast microscope/electron microscope method.

DESCRIPTION OF EMBODIMENTS

Figure 1:
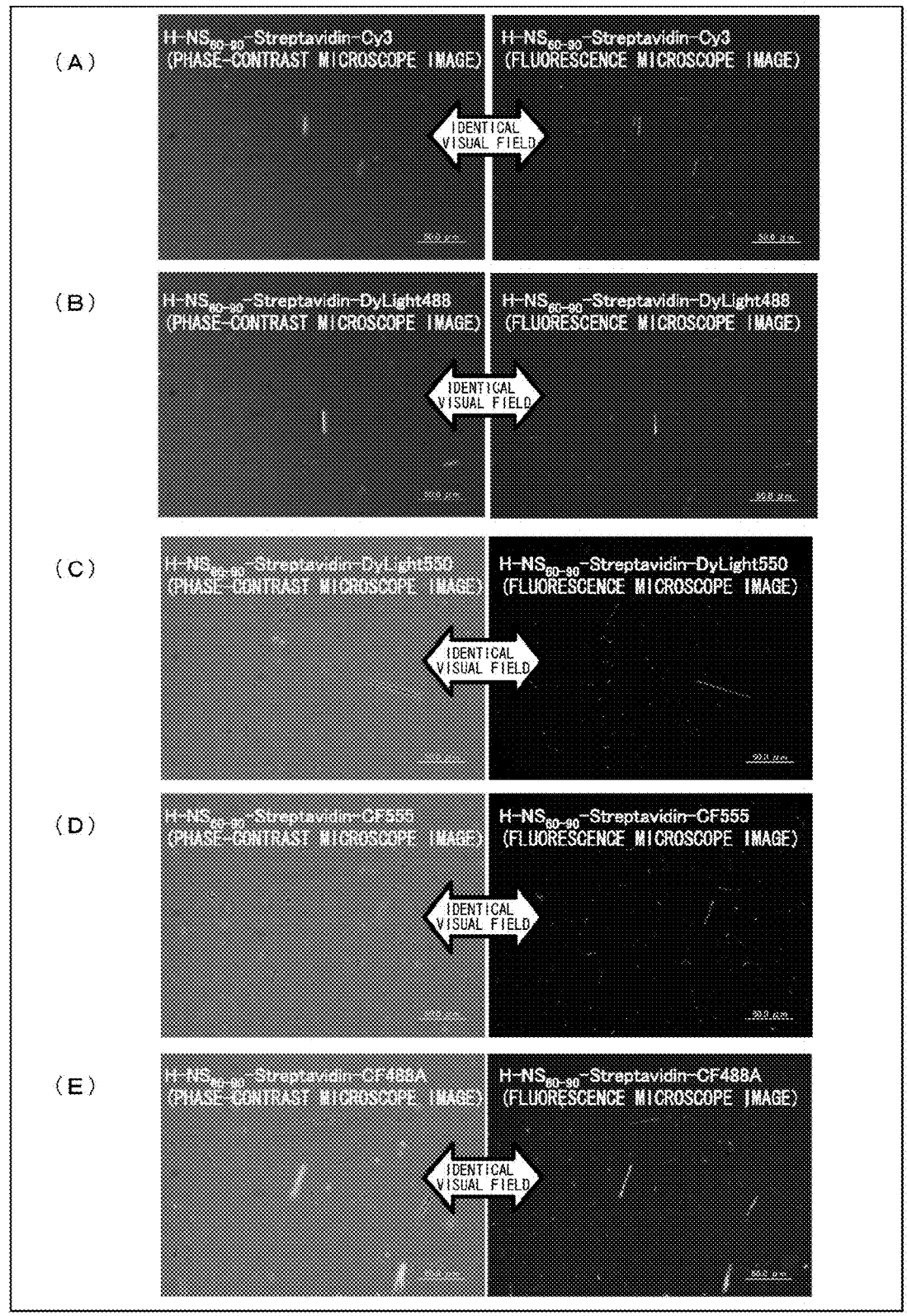
FIG. 1 is a view showing a result of asbestos microscopic observation using a phase-contrast fluorescence method.

An embodiment of the present invention is described below in details. Note, however, that the present invention is not limited to this, but may be altered in various ways within the scope of the description. The academic literatures and patent literatures described herein are hereby incorporated by reference in their entireties. Note that the numerical range "A to B" used herein means "not less than A to not more than B" unless otherwise specified.

A method of the present invention for detecting asbestos includes:

the contact step of bringing an asbestos-binding protein having a fluorescent label into contact with a test sample;

the first detection step of detecting, after the contact step, a fibrous substance contained in the test sample with use of a phase-contrast microscope; and the second detection step of detecting, with use of a fluorescence microscope, the asbestos-binding protein that has bound to the fibrous substance detected in the first detection step, the first detection step and the second detection step being carried out with an identical visual field.

The "test sample" refers to a sample which is to be examined as to whether it contains asbestos or not. Examples of the test sample encompass building materials such as mortar and rock wool, ores such as serpentine, and a sampled air in an environment where asbestos is to be detected.

A test sample in the air (atmosphere) can be collected by filtering the air in an environment to be assayed. A method for collecting a test sample with the use of a filter is not limited in particular, provided that it can collect a test sample by filtering the air in an environment to be assayed. For example, a test sample can be collected according to the method described in "Asbestos Monitoring Manual (Fourth Edition)" (Non-Patent Literature 1). The "filter" is not limited to a specific one, and can be generally, for example, a membrane filter made of cellulosic ester or a polycarbonate filter.

As described above, the test sample may be one collected with the use of a filter. In this case, it is preferable that the method of the present invention further include the transparentizing step of making the filter transparent after the contact step, so that the first detection step is carried out after the transparentizing step.

That is, in a case where asbestos detection is carried out for a test sample collected with the use of a filter, a method of the present invention for detecting asbestos includes:

the contact step of bringing an asbestos-binding protein having a fluorescent label into contact with a test sample collected with the use of a filter;

the transparentizing step of making the filter transparent after the contact step;

the first detection step of detecting, after the transparentizing step, a fibrous substance contained in the test sample with use of a phase-contrast microscope; and the second detection step of detecting, with use of a fluorescence microscope, the asbestos-binding protein that has bound to the fibrous substance detected in the first detection step, the first detection step and the second detection step being carried out with an identical visual field.

Note that "asbestos" used herein is synonymous with "Ishiwata" in Japanese.

The inventors of the present invention named this novel asbestos detection method "phase-contrast fluorescence method".

[1. Contact Step]

The "contact step" is a step of bringing an asbestos-binding protein having a fluorescent label into contact with a test sample (or a test sample collected with the use of a filter).

The "asbestos-binding protein having a fluorescent label" may be an asbestos-binding protein modified with a fluorescent substance or may be a fusion protein of a fluorescent protein and an asbestos-binding protein. Note that the "asbestos-binding protein having a fluorescent label" is sometimes referred to simply as "asbestos-binding protein". The "fluorescent label" and "asbestos-binding protein" will be described later.

A method for bringing the asbestos-binding protein and the test sample into contact with each other is not limited in particular, but it is preferable to bring the asbestos-binding protein and the test sample into contact with each other in a solution because they can be made contact with each other efficiently in a solution. For example, it is possible to add the test sample to a solution containing the asbestos-binding protein and fully blend them. Conversely, it is also possible to add the asbestos-binding protein to a suspension containing the test sample and fully blend them. Alternatively, it is also possible to mix a solution containing the asbestos-binding protein and a suspension containing the test sample and fully blend them. In the case where the test sample is collected with the use of a filter, it is possible to bring the asbestos-binding protein and the test sample into contact with each other in a solution by allowing a solution containing the asbestos-binding protein to drip onto a surface (capturing surface) of the filter on which the test sample has been collected. Note that conditions (e.g., temperature, time, etc.) for the contact between the asbestos-binding protein and the test sample are not limited in particular, provided that they can be fully made contact with each other. Preferable conditions can be employed after appropriate consideration.

An amount of the asbestos-binding protein to be brought into contact with the test sample is not limited in particular. Note, however, that in a case where the amount of the asbestos-binding protein is too small relative to the amount of the test sample, there is a risk of insufficient detection of asbestos contained in the test sample. Meanwhile, in a case where the amount of the asbestos-binding protein is excessive relative to the amount of the test sample, there is a risk of a decline in accuracy due to non-specific binding between a substance other than asbestos and the asbestos-binding protein. It is therefore preferable that the asbestos-binding protein to be brought into contact with the test sample have an amount that is unlikely to cause non-specific binding with a substance other than asbestos and allows for sufficient contact with the test sample. For example, in a case of allowing a solution containing the asbestos-binding protein to drip onto the collecting surface of the filter, it is preferable that a solution containing the asbestos-binding protein in concentration of 0.5 nM to 5 µM, preferably 5 nM to 500 nM be allowed to drip onto the collecting surface of the filter at 33 µl/cm$^2$ to 98 µl/cm$^2$, preferably 33 µl/cm$^2$ to 49 µl/cm$^2$.

The "solution" can be any solution, provided that it will not inhibit or reduce binding between the asbestos-binding protein and the test sample and reduce specificity of binding of the asbestos-binding protein to the test sample. Examples of such a solution encompass a phosphate buffer solution, carbonate buffer solution, and a tris buffer solution.

In a case where the asbestos-binding protein and the test sample are brought into contact with each other in a solution in the contact step, the solution may contain a surfactant (Tween20 (Registered Trademark), Triton X-100, etc.) in order to avoid non-specific biding. In Examples described later, the contact step is carried out by using, as the solution, a buffer solution having a composition of a 0.3M phosphate buffer solution (pH 8.0), 0.3M NaCl, and 0.5% Tween80 (Registered Trademark).

According to the method of the present invention for detecting asbestos, in the contact step, two or more different kinds of asbestos-binding proteins may be contacted with the test sample. In this case, the two or more different kinds of asbestos-binding proteins are preferably proteins that specifically bind to respective different kinds of asbestos and that have fluorescent labels emitting fluorescence of respective different wavelengths. According to the arrangement, it is possible to easily distinguish different kinds of asbestos on the basis of a difference in color of fluorescence in the subsequent second detection step.

Specifically, for example, a protein (e.g., DksA protein (database name: GenBank, accession No.: AAC73256)) that specifically binds to chrysotile and a protein (e.g., H-NS$_{60-90}$ protein (database name: GenBank, accession No.: AAC74319)) that specifically binds to amphibole asbestos are used in combination as asbestos-binding proteins, and these asbestos-binding proteins are caused to have fluorescent labels emitting fluorescence of respective different wavelengths (e.g., one of these asbestos-binding proteins is labeled with Cy3, and the other is labeled with DyLight488). This makes it possible to separately detect chrysotile and amphibole asbestos on the basis of a difference in fluorescent color in the subsequent second detection step. Note that a combination of the two or more different kinds of asbestos-binding proteins and a combination of fluorescent labels emitting fluorescence of respective different wavelengths are not limited to those described above. Proper combinations can be selected, in accordance with the kind etc. of asbestos of interest, from among every kind of asbestos-binding proteins and every kind of fluorescent labels.

For example, by labeling one asbestos-binding protein with a green fluorescent pigment and labeling the other asbestos-binding protein with a red fluorescent pigment, it is possible to separately detect chrysotile and amphibole asbestos on the basis of a difference in fluorescent color. Examples of the "green fluorescent pigment" encompass fluorescein, DyLight488, Alexa488, ATTO488, and CF488A. Examples of "red fluorescent pigment" encompass Cy3, DyLight550, and CF555. It is only necessary that one kind of these "green fluorescent pigments" and one kind of these "red fluorescent pigment" be selected and combined.

The following describes in detail the "asbestos-binding protein" and the "fluorescent label".

(1-1. Asbestos-Binding Protein)

The "asbestos-binding protein" as used herein refers to a protein having a property of specifically binding to asbestos. Whether a protein is specifically binding to asbestos or not can be judged by examining whether or not the protein to be examined binds to asbestos in a solution containing 0.1M or more sodium chloride. That is, the protein and asbestos are mixed in the solution containing 0.1M or more sodium chloride, a protein that has bound to asbestos is eluted out, and then the protein is detected by a method such as SDS-PAGE. If a protein is detected, the protein can be regarded as a protein (asbestos-binding protein) that specifically binds to asbestos (see Patent Literature 1 for details). A protein can be regarded as a protein that specifically binds to asbestos if it binds to asbestos in a solution containing 0.1M or more sodium chloride. Note, however, that it is difficult for a protein to bind to asbestos in a solution containing 0.3M or more sodium chloride, and it is therefore preferable to examine whether or not a protein to be examined binds to asbestos in a solution containing 0.1M to 0.3M, preferably 0.2M to 0.3M sodium chloride. It is, of course, possible to examine whether or not a protein to be examined binds to asbestos in a solution containing 0.3M or more sodium chloride (e.g., 0.3M to 0.5M, 0.3M to 1M, 0.5M to 1M, or 1M or more). It can be said that a protein has higher binding specificity to asbestos when it can bind to asbestos in a solution containing a higher concentration of sodium chloride.

Examples of such an asbestos-binding protein encompass an H-NS protein (database name: GenBank, accession No.: AAC74319), a DksA protein (database name: GenBank, accession No.: AAC73256), a GatZ protein (database name: GenBank, accession NO.: AAC75156), a DnaK protein (database name: GenBank, accession No.: AAC73125), an H1pA protein (database name: GenBank, accession No.: AAC73289), a YgiW protein (database name: GenBank, accession No.: AAC76060), a CspA protein (database name: GenBank, accession No.: AAN68075), a Cg10974 protein (database name: GenBank, accession No.: BAB98367), an OmpC protein (database name: GenBank, accession No.: AAC75275), an OmpA protein (database name: GenBank, accession No.: AAC74043), a S1 protein (database name: GenBank, accession No.: AAC73997), a S4 protein (database name: GenBank, accession No.: AAC76321), an L1 protein (database name: GenBank, accession No.: AAC76958), an L5 protein (database name: GenBank, accession No.: AAC76333), an L7 protein (database name: GenBank, accession No.: AAC76960), and a TTC0984 protein (database name: NCBI, accession No.: YP_004953). Note, however, that the present invention is not limited to these. These asbestos-binding proteins may be used alone or may be used in combination of two or more kinds.

The amino acid region from the 1st to 57th amino acids (SEQ ID NO:7) of the "H-NS protein" can specifically bind to chrysotile (white asbestos). The amino acid region from the 60th to 90th amino acids (SEQ ID NO:8) can specifically bind to amosite (brown asbestos), crocidolite (blue asbestos), anthophylite, toremolite, and actinolite.

The "DksA protein" can specifically bind to chrysotile (white asbestos).

The "GatZ protein" can specifically bind to amosite (brown asbestos), crocidolite (blue asbestos), anthophylite, toremolite, and actinolite.

The "DnaK protein" can specifically bind to chrysotile (white asbestos).

The "H1pA protein" can specifically bind to chrysotile (white asbestos).

The "YgiW protein" can specifically bind to chrysotile (white asbestos).

The "CspA protein" can specifically bind to chrysotile (white asbestos).

The "Cg10974 protein" can specifically bind to chrysotile (white asbestos).

The "S4 protein" can specifically bind to amosite (brown asbestos) and crocidolite (blue asbestos).

The "L1 protein" can specifically bind to amosite (brown asbestos) and crocidolite (blue asbestos).

The "L5 protein" can specifically bind to amosite (brown asbestos) and crocidolite (blue asbestos).

The L7 protein" can specifically bind to amosite (brown asbestos) and crocidolite (blue asbestos).

The "OmpC protein" can specifically bind to chrysotile (white asbestos), amosite (brown asbestos), and crocidolite (blue asbestos).

The "OmpA protein" can specifically bind to chrysotile (white asbestos), amosite (brown asbestos), and crocidolite (blue asbestos).

The "S1 protein" can specifically bind to chrysotile (white asbestos), amosite (brown asbestos), and crocidolite (blue asbestos).

The "TTC0984 protein" can specifically bind to amosite (brown asbestos) and crocidolite (blue asbestos).

In a case where asbestos detection is carried out for a test sample collected with the use of a filter, it is necessary to make the filter transparent. It is therefore preferable that an asbestos-binding protein used in this case be a protein whose binding with asbestos is maintained after a transparentizing step (described later). By using an asbestos-binding protein having such a property, it is possible to detect asbestos even after the transparentizing step. Whether "binding with asbestos is maintained after a transparentizing step" can be judged by examining a change in amount of the asbestos-binding protein binding to asbestos before and after the transparentizing step. For example, assuming that an intensity of fluorescence (fluorescence intensity) of a fluorescently-labeled protein binding to asbestos (asbestos-binding protein having a fluorescent label) is 100% before the transparentizing step, a protein which can be regarded as a protein whose binding with asbestos is maintained after the transparentizing step is a protein whose fluorescence intensity is maintained at preferably 20% or more, more preferably 50% or more, further more preferably 80% or more after the transparentizing step-transparentizing step. The fluorescence intensity can be measured by a known method by using, for example, a fluorescence microscope.

As described later, since fluorescence intensities of some kinds of fluorescent labels are influenced by the transparentizing step, a fluorescent label used to examine an amount of an asbestos-binding protein binding to asbestos is one whose fluorescence can be detected by a fluorescence microscope after the transparentizing step. The amount of the asbestos-binding protein binding to asbestos is finally determined by taking into account how much a fluorescence intensity of the fluorescent label is influenced by the transparentizing step.

Examples of an asbestos-binding protein whose binding with asbestos is maintained after the transparentizing step encompass an H-NS protein (database name: GenBank, accession No.: AAC74319), a DksA protein (database name: GenBank, accession No.: AAC73256), and a GatZ protein (database name: GenBank, accession NO.: AAC75156). Note, however, that the present invention is not limited to these. These asbestos-binding proteins may be used alone or may be used in combination of two or more kinds.

An organism from which the asbestos-binding protein is derived is not limited in particular, and may be any organism such as a bacterium, a yeast, a plant, or an animal.

As used herein, the term "protein" is interchangeable with "polypeptide" or "peptide". The term "protein" encompasses a partial segment (fragment) of a protein. Further, the term "protein" encompasses a fusion protein. The "fusion protein" is a protein formed through binding between parts (fragments) or all of two more heterologous proteins.

The asbestos-binding protein used in the present invention may also be a protein which consists of an amino acid sequence having deletion, substitution, and/or addition of one or several amino acids in the above-exemplified amino acid sequences and which can bind to asbestos.

What is meant by "deletion, substitution, and/or addition of one or several amino acids" is deletion, substitution, and/or addition of amino acids the number of which is the number of amino acids that can be deleted, substituted, and/or added by a known mutant peptide producing method such as a site-specific mutagenesis (e.g., 5% or less of the total number of amino acids). The number of amino acids that are deleted, substituted, and/or added is not limited in particular, provided that it is 5% or less of the total number of amino acids and a protein obtained after the deletion, substitution, and/or addition of the amino acids has activity of binding to asbestos.

A site where one or several amino acids are deleted, substituted, and/or added can be any site of the amino acid sequence, provided that a protein obtained after the deletion, substitution, and/or addition of the amino acids has activity of binding to asbestos.

Such a mutant polypeptide is not limited to a polypeptide that is artificially mutated by a known mutant polypeptide producing method, and it may be obtained by isolating and purifying naturally occurring similar mutant polypeptides.

It is well known in the art that some amino acids in an amino acid sequence of a protein can easily be modified without significantly affecting the structure or function of the protein. It is also well known that such a mutant with no significant structural or functional change occurs not only in artificially modified proteins but in nature as well.

The mutant preferably includes substitution, deletion, or addition of amino acids, which may be conservative or non-conservative. Silent substitution, silent addition, and silent deletion are preferable, and conservative substitution is especially preferable. Neither of these modifications changes the polypeptide activities in the present invention.

Representative examples of conservative substitution encompass: substitution of one of aliphatic amino acids Ala, Val, Leu, and Ile with another amino acid; exchange of hydroxyl residues Ser and Thr; exchange of acidic residues Asp and Glu; substitution between amide residues Asn and Gln; exchange of basic residues Lys and Arg; and substitution between aromatic residues Phe and Tyr.

The asbestos-binding protein used in the present invention may include an additional peptide. An example of an additional peptide is polyarginine tag (Arg-tag), polyhistidine tag (His-tag), or an epitope-labeled peptide such as Myc or Flag.

The asbestos-binding protein used in the present invention is not limited in particular, provided that it can specifically bind to asbestos. It is therefore possible for a person skilled in the art to easily understand whether or not even a protein other than the above-exemplified proteins can be used in the present invention, by examining whether or not the protein can specifically bind to asbestos.

Similarly, a person skilled in the art can easily understand whether or not even a protein other than the above-exemplified proteins is a protein whose binding with asbestos is maintained after the transparentizing step, by examining whether or not binding with asbestos can be maintained after the transparentizing step.

The asbestos-binding protein used in the present invention may be a partial peptide including a part of an entire amino acid sequence of an asbestos-binding protein which part contributes to binding with asbestos. For example, in Examples that will be described later, a partial peptide, which is the amino acid region from the 60th to 90th amino acids of the H-NS protein is used. Use of such a partial peptide makes it possible to improve specificity of an asbestos-binding protein to asbestos (especially amosite (brown asbestos), crocidolite (blue asbestos), anthophylite, toremolite, actinolite).

The asbestos-binding protein used in the present invention is preferably multimerized from the viewpoint of stronger binding between asbestos and the asbestos-binding protein. That is, the asbestos-binding protein used in the present invention is preferably a multimeric protein.

The "multimeric protein" refers to a protein obtained by covalent bonding such as disulfide bonding or non-covalent bonding of two or more proteins (polypeptides). In a case where a protein is a multimer (e.g., dimer), the protein can bind to asbestos via a plurality of proteins. This achieves stronger binding between the asbestos-binding protein and asbestos as compared with binding with asbestos via a single protein.

A method for producing a multimeric protein is not limited in particular, and can be a known method. In Examples that will be described later, fusion proteins of streptavidin and a partial peptide, which is the amino acid regions from the 60th to 90th amino acids of the H-NS protein, are produced, so that these fusion proteins are tetramerized by utilizing a streptavidin's property of forming a tetramer.

The asbestos-binding protein used in the present invention can be produced by culturing cells as a supply source of the protein, and isolating and purifying the protein from the cell. Also, the asbestos-binding protein used in the present invention can be produced by constructing a recombinant expression vector by a known genetic engineering technique, and introducing the recombinant expression vector into an appropriate host cell to express a recombinant protein. Also, the asbestos-binding protein used in the present invention can be produced by chemical synthesis using an amino acid synthesizer.

(1-2. Fluorescent Label)

As used herein, the "fluorescent label" refers to a substance which allows a protein binding to asbestos to be detected based on fluorescence so that asbestos can be detected with the use of the asbestos-binding protein. Since a fluorescent label exhibits fluorescence when it exists, it is possible to easily determine presence or absence of an asbestos-binding protein by observation under a fluorescence microscope. It is therefore possible to easily detect asbestos.

The "fluorescent label" is not limited in particular, provided that its fluorescence can be detected with the use of a fluorescence microscope. The "fluorescent label" can be appropriately selected from existing fluorescent substances, fluorescent proteins, and the like.

As used herein, the "fluorescent substance" refers to a non-protein low-molecular fluorescent compound. The "fluorescent substance" is not limited in particular, provided that its fluorescence can be detected with the use of a fluorescence microscope. Examples of the "fluorescent substance" encompass Cy3, DyLight488, fluorescein, Alexa488, ATTO488, CF488A, DyLight550, and CF555. Other examples of the "fluorescent substance" encompass green fluorescent pigments (e.g., Cy2, rhodamine green) red fluorescent pigments (e.g., rhodamine, Cy5, Alexa546, Alexa555, Alexa568, Alexa594, CF568, CF594, DY547). Note, however, that the present invention is not limited to this. These fluorescent substances may be used alone or may be used in combination of two or more kinds.

The "fluorescent protein" can be, for example, a green fluorescent protein (GFP). Where the "fluorescent protein" is derived from is not limited in particular.

In a case where asbestos detection is carried out for a test sample collected with the use of a filter, it is necessary to make the filter transparent. Therefore, a "fluorescent label" used in this case is not limited in particular, provided that its fluorescence can be detected with the use of a fluorescence microscope after the transparentizing step (described later). Assuming that an intensity of fluorescence (fluorescence intensity) emitted by a fluorescent label before the transparentizing step is 100%, it is preferable, from the viewpoint of improved asbestos detection sensitivity, to use a fluorescent label whose fluorescence intensity is maintained at preferably 20% or more, more preferably 50% or more, further more preferably 80% or more after the transparentizing step.

A fluorescence intensity of a fluorescent label can be measured by a known method. For example, a fluorescence intensity can be evaluated by measuring luminance. Specifically, a ratio of maintenance of a fluorescence intensity can be calculated by measuring luminance with the use of image analysis software VH Analyzer (KEYENCE). By using a fluorescent label having such a fluorescence intensity, it is possible to accurately detect asbestos even after the transparentizing step.

The fluorescent label whose fluorescence can be detected with the use of a fluorescence microscope after the transparentizing step can be appropriately selected from existing fluorescent substances, fluorescent proteins, and the like. Examples of such a fluorescent label encompass Cy3, DyLight488, fluorescein, Alexa488, ATTO488, CF488A, DyLight550, and CF555. Note, however, that the present invention is not limited to these. These fluorescent substances may be used alone or may be used in combination of two or more kinds.

A person skilled in the art can easily understand whether or not even a fluorescent label other than the above exemplified fluorescent labels is a fluorescent label whose fluorescence can be detected with the use of a fluorescence microscope after the transparentizing step, by examining whether or not the fluorescence can be detected with the use of the fluorescence microscope after the transparentizing step.

The fluorescent label can be bound to an asbestos-binding protein by a labeling method suitable for the fluorescent label. For example, an asbestos-binding protein can be labeled with the use of a commercially available kit etc. for labeling a protein.

In a case where an asbestos-binding protein is labeled with a fluorescent substance, the asbestos-binding protein can be labeled with the fluorescent substance by utilizing chemical bonding.

In a case where an asbestos-binding protein is labeled with a fluorescent protein, a fusion protein of the fluorescent protein and the asbestos-binding protein can be expressed as a recombinant protein by a known genetic engineering method. In this case, it is possible to use a method of artificially coupling a gene encoding the asbestos-binding protein with a gene encoding the fluorescent protein to produce a fusion gene, inserting the fusion gene into a downstream of a promoter of an expression vector, and introducing the expression vector into a host cell such as *Escherichia coli* to express the fusion gene.

Some asbestos-binding proteins become insoluble after being fluorescently labeled. One reason for this is that a molecular weight of the asbestos-binding proteins becomes too large by the labeling. In such a case, it is effective to use a fluorescent substance with a relatively small molecular weight as a fluorescent label.

In order to further improve asbestos detection sensitivity, it is preferable to use, as the fluorescent label, a substance having a high fluorescence intensity and a high stability. Use of such a fluorescent label makes it possible to improve asbestos detection sensitivity. It is therefore possible to detect asbestos even in a case where an amount of asbestos contained in a test sample is small.

[2. Detection Step]

The method of the present invention for detecting asbestos includes the following detection steps (i) and (ii):

(i) the first detection step of detecting, after the contact step (in some cases, after the transparentizing step), a fibrous substance contained in the test sample with the use of a phase-contrast microscope, and (ii) the second detection step of detecting, with the use of a fluorescence microscope, an asbestos-binding protein that has bound to the fibrous substance detected in the first detection step.

The first detection step and the second detection step are herein referred to collectively as "detection steps". According to the method of the present invention for detecting asbestos, a detection object can be observed by switching, as needed, between the phase-contrast microscope and the fluorescence microscope any number of times. Therefore, according to the method of the present invention for detecting asbestos, the first detection step and the second detection step can be repeated at least one time. That is, it is possible that the second detection step be carried out after the first detection step and then the first detection step be carried out again.

Specifically, it is for example possible that the first detection step be carried out again after the second detection step so that a shape (length, width, and a length-width ratio) of a fibrous substance whose binding to the asbestos-binding protein has been detected by the fluorescence microscope is examined again. By thus repeating the first detection step and the second detection step at least one time, it is possible to more surely detect asbestos.

Alternatively, it is for example possible that (i) every time a single fibrous substance contained in the test sample is detected, the second detection step be carried out to detect an asbestos-binding protein that has bound to this fibrous substance and then (ii) the first detection step be carried out again to detect another fibrous substance contained in the test sample. By thus carrying out the second detection step every time a single fibrous substance is detected in the first detection step, it is possible to efficiently detect asbestos with an identical visual field.

It is of course possible that after all fibrous substances contained in the test sample are detected in the first detection step, the second detection step be carried out for the fibrous substances thus detected.

As described above, according to the method of the present invention for detecting asbestos, it is possible to observe a detection object by switching, as needed, between the phase-contrast microscope and the fluorescence microscope any number of times (for example, detection using the phase-contrast microscope is carried out again after the detection using the fluorescence microscope). This makes it possible to more surely detect asbestos.

Note, however, that the second detection step must be carried out after the first detection step. In the case where the second detection step is carried out after the first detection step, fine asbestos fibers that cannot be detected by a phase-contrast microscope are excluded by the first detection step, and therefore there is no risk that such asbestos fibers are observed as asbestos in the second detection step. That is, there is no risk that the total number of asbestos finally detected according to the method of present invention for detecting asbestos exceeds the total number of asbestos detected in a case where the same sample is examined by a phase-contrast microscope.

Moreover, according to the method of present invention for detecting asbestos, the first detection step and the second detection step are carried out with an identical visual field.

According to the method of present invention for detecting asbestos with the use of phase-contrast/fluorescence microscopes or the like, the first detection step and the second detection step can be carried out without changing a visual field just by switching a light path from transmitting light for phase-contrast observation to epifluorescence. By thus carrying out the first detection step and the second detection step with an identical visual field, that is, by shifting to the second detection step from the first detection step with the visual field kept as it is, by just switching a light path of the microscope from its phase-contrast mode to its fluorescence mode after narrowing down a detection object with the use of a phase-contrast microscope in the first detection step, it is possible to carry out the second detection step without changing the visual field. This makes it possible to instantly determine whether each of the fibrous substances detected in the first detection step is asbestos or not.

The following describes the "first detection step" and the "second detection step".

(2-1. First Detection Step)

The "first detection step" is a step of detecting, after the contact step (in some cases, after the transparentizing step), a fibrous substance contained in the test sample with the use of a phase-contrast microscope.

As used herein, the "fibrous substance" is not limited in particular provided that it is a substance having a fibrous portion, and may be one whose fibrous portion is branched or may be one whose fibrous portion has particles attached thereto. Details of a criterion of the "fibrous substance" are described in "Asbestos Monitoring Manual (Fourth Edition)" (Non-Patent Literature 1).

In the first detection step, it is only necessary that the "fibrous substance" be detected based on a fibrous substance detection criterion of phase-contrast microscopy. Fibrous substances that meet the fibrous substance detection criterion of phase-contrast microscopy are, for example, fibrous substances that satisfy the following conditions: length of 5 µm or more, width of less than 3 µm, and a length-width ratio of 3:1 or more (see "Asbestos Monitoring Manual (Fourth Edition)" (Non-Patent Literature 1)). That is, according to the method of the present invention for detecting asbestos, it is preferable that a fibrous substance having a length of 5 µm or more, width of less than 3 µm, and a length-width ratio of 3:1 or more be detected in the first detection step in compliance with the current detection criterion of the phase-contrast microscopy.

The "length" of the fibrous substance can be determined relatively easily, for example, by utilizing a graticule of an eyepiece attached to an eyepiece lens. Note, however, that a method for determining the "length" of the fibrous substance is not limited to this.

The "width" of the fibrous substance is interchangeable with "diameter" of the fibrous substance. The "diameter" refers to a diameter of a circle in which the fibrous substance is inscribed. The "width" of the fibrous substance can be determined relatively easily, for example, by utilizing a graticule of an eyepiece attached to an eyepiece lens. Note, however, that a method for determining the "width" of the fibrous substance is not limited to this.

The "length-width ratio" of the fibrous substance is interchangeable with "aspect ratio" of the fibrous substance.

The "length", "width", and "length-width ratio" of the fibrous substance are specified in details in "Asbestos Monitoring Manual (Fourth Edition)" (Non-Patent Literature 1). The "length", "width", and "length-width ratio" of the fibrous substance can be determined according to the method specified in this literature.

Note, however, that the fibrous substance detection criterion in the method of the present invention for detecting asbestos is not limited to the above criterion. In a case where the fibrous substance detection criterion of phase-contrast microscopy is changed, it is only necessary to carry out the method of the present invention for detecting asbestos so that a fibrous substance is detected based on a new fibrous substance detection criterion of phase-contrast microscopy. Since, according to the method of the present invention for detecting asbestos, a fibrous substance is detected in the first detection step based on the fibrous substance detection criterion of phase-contrast microscopy, it is possible to detect asbestos without changing the asbestos detection criterion of the phase-contrast microscope/electron microscope method.

According to the method of present invention for detecting asbestos, first, a predetermined fibrous substance contained in a test sample collected with the use of a filter is detected with the use of a phase-contrast microscope in the first detection step, so that a detection object in the subsequent second detection step is narrowed down. This eliminates a risk of detection, in the second detection step using the bio-fluorescence method, of fine asbestos fibers that cannot be detected by the phase-contrast microscope/electron microscope method. That is, there is no risk of occurrence of a situation in which the total number of asbestos finally detected according to the method of present invention for detecting asbestos exceeds the total number of asbestos detected in a case where the same sample is examined by the phase-contrast microscope/electron microscope method. It is therefore possible to detect asbestos without changing the asbestos detection criterion of the conventional method.

(2-2. Second Detection Step)

The "second detection step" is a step of detecting, with the use of a fluorescence microscope, the asbestos-binding protein that has bound to the fibrous substance detected in the first detection step.

In the second detection step, the fluorescent label possessed by the asbestos-binding protein is detected with the use of the fluorescence microscope. This makes it possible to easily detect the asbestos-binding protein that has bound to the fibrous substance detected in the first detection step. Specifically, in a case where fluorescence can be confirmed in the fibrous substance detected in the first detection step under the fluorescence microscope, it can be determined that the asbestos-binding protein is bound to the fibrous substance, whereas in a case where no fluorescence can be confirmed, it can be determined that no asbestos-binding protein is bound to the fibrous substance. It can be determined that the fibrous substance to which the asbestos-binding protein is bound is asbestos, whereas it can be determined that the fibrous substance to which no asbestos-binding protein is bound is not asbestos.

A method for detecting a fluorescent label with the use of a fluorescence microscope is not limited in particular. Preferable conditions can be employed after appropriate consideration of a detection method (excitation wavelength etc.) suitable for a fluorescent label to be detected.

Configurations of the phase-contrast microscope and the fluorescence microscope used in the respective detection steps are not limited in particular. For example, a microscope (phase-contrast/fluorescence microscope) including a capacitor for a phase-contrast microscope and an epifluorescent device or a polarized light microscope including these two can be used as a microscope. This makes it possible to carry out the detection steps without changing a visual field just by switching a light path from transmitting light for phase-contrast observation to epifluorescence. That is, use of such a microscope as a phase-contrast/fluorescence microscope makes it possible to carry out the second detection step by narrowing down a detection object with the use of a phase-contrast microscope and then just switching a light path of the microscope from the phase-contrast mode to the fluorescence mode. This makes it possible to instantly determine in the second detection step whether each of the fibrous substances detected in the first detection step is asbestos or not.

[3. Transparentizing Step]

The "transparentizing step" is a step of making the filter transparent after the contact step. By making the filter transparent in the transparentizing step, it is possible to detect a fibrous substance contained in a test sample under a phase-contrast microscope in the subsequent first detection step in a case where the test sample is collected with the use of the filter. A method for making a filter transparent (colorless) is not limited in particular, provided that it is a method for making the filter transparent to such a degree that the fibrous substance can be detected under a phase-contrast microscope in the subsequent first detection step. One example of such a method is a method of spraying an acetone vapor upon the filter until the filter becomes transparent. This method is described in detail in "Asbestos Monitoring Manual (Fourth Edition)" (Non-Patent Literature 1). Another example of such a method is a method using a DMF solution [DMF (Dimethyl formamide) 35%, water 50%, acetic acid 15%]. This method is described in detail in "Asbestos Monitoring Manual (Fourth Edition)" (Non-Patent Literature 1).

Note that in a case where the transparentizing step is carried out, the transparentizing step is always carried out after the contact step since the test sample collected by the filter cannot be made contact with the asbestos-binding protein after the transparentizing step.

[4. Other]

The method of the present invention for detecting asbestos may include a step other than the above steps. For example, the method of the present invention for detecting asbestos may include, before the contact step, the collecting step of collecting a test sample by filtering air in an environment to be assayed. Furthermore, the method of the present invention for detecting asbestos may include the step of calculating an asbestos concentration in the test sample on the basis of a result obtained through the series of detection steps or the step of calculating an asbestos concentration in the environment to be assayed on the basis of a result obtained through the series of detection steps.

As described above, according to the method of the present invention for detecting asbestos, it is possible to more efficiently, easily and accurately detect asbestos without changing an asbestos detection criterion used in the conventional method, as compared with the phase-contrast microscope/electron microscope method.

The present invention can also be arranged as follows.

In the method of present invention for detecting asbestos, it is preferable that the test sample is collected with use of a filter; the method further comprises the transparentizing step of making the filter transparent after the contact step; and the first detection step is carried out after the transparentizing step.

As described above, according to the method of present invention for detecting asbestos, a phase-contrast microscope and a fluorescence microscope are used in combination to detect asbestos. More specifically, in the first detection step, a predetermined fibrous substance is first detected under the phase-contrast microscope, and then the fibrous substance is subjected to the bio-fluorescence method in the second detection step. In a case where a test sample is collected with the use of a filter (e.g., a case where asbestos in the atmosphere is to be detected), the phase-contrast microscope and the fluorescence microscope can be used in combination by making the filter on which the test sample is collected transparent in the transparentizing step. The transparentizing step needs to be carried out after the contact step. This is because after the transparentizing step, the filter cannot transmit a solution and cannot be washed, and therefore the contact step cannot be fully carried out.

According to the arrangement, it is therefore possible to detect asbestos in the atmosphere more efficiently, easily and accurately without changing the asbestos detection criterion of the phase-contrast microscope/electron microscope method, as compared with the phase-contrast microscope/electron microscope method.

In the method of the present invention for detecting asbestos, it is preferable that the first detection step and the second detection step are repeated at least one time.

According to the method of present invention for detecting asbestos, a detection object can be confirmed by switching the phase-contrast microscope and the fluorescence microscope any number of times. It is thus possible to confirm a detection object by switching, as needed, the phase-contrast microscope and the fluorescence microscope any number of times. For example, detection under the phase-contrast microscope can be carried out again after detection under the fluorescence microscope. As a result, it is possible to more surely detect asbestos.

In the method of the present invention for detecting asbestos, it is preferable that the first detection step is a step of detecting a fibrous substance having a length of 5 μm or more, a width of less than 3 μm, and a length-width ratio of 3:1 or more.

According to the arrangement, fibrous substances that are 5 μm or more in length, less than 3 μm in width, and 3:1 or more in length-width ratio are detected in the first detection step in accordance with the current criterion of the phase-contrast microscope method. Accordingly, there is no risk of occurrence of a situation in which the total number of asbestos finally detected by the method of present invention for detecting asbestos exceeds the total number of asbestos detected in a case where the same sample is examined by a phase-contrast microscope. It is therefore possible to detect asbestos without changing the current asbestos detection criterion of the phase-contrast microscope/electron microscope method.

In the method of the present invention for detecting asbestos, it is preferable that the asbestos-binding protein is a protein whose binding with asbestos is maintained after the transparentizing step; and the fluorescent label is one whose fluorescence is detectable by the fluorescence microscope after the transparentizing step.

According to the arrangement, it is possible to accurately detect asbestos even after the transparentizing step.

In the method of the present invention for detecting asbestos, it is preferable that the asbestos-binding protein is at least one protein selected from the group consisting of an H-NS protein, a DksA protein, and a GatZ protein.

According to the arrangement, it is possible to accurately detect asbestos even after the transparentizing step.

In the method of the present invention for detecting asbestos, it is preferable that the fluorescent label is at least one fluorescent substance selected from the group consisting of Cy3, DyLight488, fluorescein, Alexa488, ATTO488, CF488A, DyLight550 and CF555.

According to the arrangement, it is possible to accurately detect asbestos even after the transparentizing step.

In the method of the present invention for detecting asbestos, it is preferable that the asbestos-binding protein is a multimer of at least one protein selected from the group consisting of the H-NS protein, the DksA protein, and the GatZ protein.

In a case where the asbestos-binding protein is a multimeric protein, it is possible to achieve stronger binding power between asbestos and the asbestos-binding protein as compared with a case where the asbestos-binding protein binds to asbestos via a single protein. According to the arrangement, it is therefore possible to detect asbestos with high sensitivity even after the transparentizing step.

In the method of the present invention for detecting asbestos, it is preferable that in the contact step, as the asbestos-binding protein, two or more different kinds of asbestos-binding proteins are brought into contact with the test sample; and the two or more different kinds of asbestos-binding proteins are proteins that specifically bind to respective different kinds of asbestos and have fluorescent labels emitting fluorescence of respective different wavelengths.

According to the arrangement, it is possible to easily distinguish different kinds of asbestos on the basis of a difference in color of fluorescence.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following more specifically describes the present invention by using Examples. Note, however, that the present invention is not limited by Examples.

Example 1

Preparation of Asbestos-Binding Protein $H\text{-}NS_{60\text{-}90}$ and Fluorescent Label A biotin-modified asbestos-binding protein was caused to bind to fluorescently-labeled streptavidin by using biotin-streptavidin interaction to produce a fluorescently-labeled asbestos-binding protein.

First, a biotinylated asbestos-binding protein was produced. Inverse PCR was carried out with the use of an oligonucleotide primer P1 (GCTCAGAAAATCGAATGGCAC-GAACACCACCACCACCAC TGAACTA: SEQ ID NO:1) and an oligonucleotide primer P2 (CTCGAAGAT-GTCGTTCAGACCGCCACCCTCGAGTGCGGCCG CAAGCTTGTC: SEQ ID NO:2) by using a protein expression vector pET21-b (Novagen) as a template to insert biotinylated Tag at a position preceding HisTag of pET21-b. The inverse PCR was carried out with the use of KOD-plus-Mutagenesis Kit (TOYOBO) in accordance with TOYOBO's protocol. This biotinylated protein expression vector was named "pET21-AviTag-C".

Next, PCR was carried out with the use of an oligonucleotide primer P3 (CATATGCAATATCGCGAAATGCT-GATC: SEQ ID NO:3) and an oligonucleotide primer P4 (GGATCCAAACAACGTTTAGCTTTGGTGCC: SEQ ID NO:4) by using genome DNA of an E. coli K-12 strain (Escherichia coli K12, ATCC 700926) as a template to amplify a gene encoding the amino acid region between 60th to 90th amino acids (SEQ ID NO:8) of the H-NS protein (database name: GenBank, accession No.: AAC74319) which is an asbestos-binding protein. The PCR was carried out with the use of a KOD-plus Neo DNA polymerase (TOYOBO) in accordance with TOYOBO's protocol.

A PCR amplification product thus produced and the biotinylated protein expression vector pET21-AviTag-C were treated with the use of restriction enzymes NdeI and BamHI at 37° C. for 1 hour, and subjected to agarose gel electrophoresis. A DNA fragment in cut-out-gel of the agarose gel electrophoresis was ligated with the use of Ligation High (TOYOBO) at 16° C. for 30 minutes and transform the E. coli JM109 strain with the ligated. From a colony of the transformed E. coli JM109 strain, a plasmid into which a target DNA fragment was inserted was extracted. This plasmid was named "pET-H-NS$_{60-90}$-AviTag-C".

E. coli BL21 (DE3) pBirA (Novagen) transformed with the use of the pET-H-NS$_{60-90}$-AviTag-C plasmid was cultured overnight at 37° C. with the use of a 2×YT medium, and 1% (v/v) of a culture thus obtained was inoculated into a 200 ml TYH medium [20 g/l tryptone, 10 g/l yeast extract, 11 g/l HEPES, 5 g/l NaCl, 1 g/l magnesium sulfate, 0.5% glucose; adjusted to pH 7.2 to 7.4 with the use of potassium hydroxide]. After culturing at 37° C. until OD$_{600}$ becomes 0.6, IPTG (isopropyl-β-D-thioglactopyranoside) (final concentration: 0.5 mM) and D-biotin (final concentration: 100 μM) were added, and a mixture was cultured at 28° C. for 4 hours. Bacteria thus cultured were collected by centrifugation of a culture solution.

To a bacteria pellet thus obtained, 10 ml of a buffer solution A [0.05M Tris-HCl (pH 8.3), 0.05M NaCl, 10% glycerol] was added to suspend the bacteria, and the bacteria was crushed by ultrasonic waves. A cell breakage solution thus obtained was supplied to a Histrap FF column (GE Healthcare Bioscience), so as to adsorbed to the column a biotinylated H-NS$_{60-90}$ protein having histidine at its C-terminus. Then, the biotinylated H-NS$_{60-90}$ protein was eluted out from the column with the use of a buffer solution B [0.05M Tris-HCl (pH 8.3), 0.05M NaCl, 10% glycerol, 0.5M imidazole]. Polyacrylamide electrophoresis was performed with the biotinylated H—NS$_{60-90}$ protein thus obtained. The polyacrylamide electrophoresis shows that a degree of purification of the biotinylated H-NS$_{60-90}$ protein thus obtained was 95% or more.

Next, the asbestos-binding protein (H-NS$_{60-90}$ protein) was fluorescently labeled. To accomplish the fluorescent modification, the biotin modified asbestos-binding protein was caused to bind to fluorescently-labeled streptavidin by using biotin-streptavidin interaction. After 2.7 μl of the biotinylated H-NS$_{60-90}$ protein (495 μM) and 4 μl of a fluorescently-modified streptavidin solution (1 mg/ml) were mixed, a mixture thus obtained was cultured at the room temperature for 1 hour to allow the H-NS$_{60-90}$ protein to bind to fluorescently-modified streptavidin and to be fluorescently-labeled. Through this operation, a complex of the H-NS$_{60-90}$ protein and the fluorescently-labeled streptavidin was obtained. The H-NS$_{60-90}$ protein fluorescently modified with the use of streptavidin (invitrogen) labeled with a fluorescent pigment Cy3 was named "H-NS$_{60-90}$-Streptavidin-Cy3". The H-NS$_{60-90}$ protein fluorescently modified with the use of streptavidin (Thermo Scientific) labeled with a fluorescent pigment DyLight488 was named "H-NS$_{60-90}$-Streptavidin-DyLight488". The H-NS$_{60-90}$ protein fluorescently modified with the use of streptavidin (Thermo Scientific) labeled with a fluorescent pigment DyLight550 was named "H-NS$_{60-90}$-Streptavidin-DyLight550". The H-NS$_{60-90}$ protein fluorescently modified with the use of streptavidin (Biotium) labeled with a fluorescent pigment CF555 was named "H-NS$_{60-90}$-Streptavidin-CF555". The H-NS$_{60-90}$ protein fluorescently modified with the use of streptavidin (Biotium) labeled with a fluorescent pigment CF488A was named "H-NS$_{60-90}$-Streptavidin-CF488A".

The "H-NS$_{60-90}$-Streptavidin-Cy3", "H-NS$_{60-90}$-Streptavidin-DyLight488", "H-NS$_{60-90}$-Streptavidin-DyLight550", "H-NS$_{60-90}$-Streptavidin-CF555", and "H-NS$_{60-90}$-Streptavidin-CF488A" were produced by utilizing a fusion protein of streptavidin and the asbestos-binding protein, and were therefore tetramers due to the function of streptavidin. That is, the "H-NS$_{60-90}$-Streptavidin-Cy3", "H-NS$_{60-90}$-Streptavidin-DyLight488", "H-NS$_{60-90}$-Streptavidin-DyLight550", "H-NS$_{60-90}$-Streptavidin-CF555", and "H-NS$_{60-90}$-Streptavidin-CF488A" were each a tetrameric protein which was formed through polymerization of four H-NS$_{60-90}$ proteins and which was labeled with a fluorescent pigment.

Example 2

Microscopic Observation of Asbestos by Phase-Contrast Fluorescence Method (1)

A membrane filter on which amosite (brown asbestos) (JAWE231) serving as a test sample was collected was cut into a ⅛ piece, and 20 μl of a buffer solution C [0.3M phosphate buffer solution (pH8.0), 0.3M NaCl, 0.5% Tween80 (Registered Trademark)] was allowed to drip onto the ⅛ piece three times with its collecting surface facing upward.

Next, the buffer solution C (20 μl) containing, as a fluorescent protein, H-NS$_{60-90}$-Streptavidin-Cy3 (12.5 nM), H-NS$_{60-90}$-Streptavidin-DyLight488 (50 nM), H-NS$_{60-90}$-Streptavidin-DyLight550 (12.5 nM), H-NS$_{60-90}$-Streptavidin-CF555 (12.5 nM), or H-NS$_{60-90}$-Streptavidin-CF488A (50 nM) was dripped onto the ⅛ piece five times so as to cause the fluorescent protein to bind to amosite. Then, 20 μl of the buffer solution C was dripped onto the ⅛ piece three times so as to remove an unbound fluorescent protein. Finally, 20 μl of water was dripped onto the ⅛ piece three times so as to remove buffer-solution-derived surfactant and salt.

Next, the filter was placed on a slide glass (manufactured by MATSUNAMI, MICRO SLIDE GLASS, borosilicate glass with polished edges, thickness: 1 mm) with its collecting surface facing upward, and was then dried well. After drying, the filter was made transparent through application of an acetone vapor with its collecting surface facing upward. Then, a cover glass (manufactured by MATSUNAMI, 18×18 mm) was placed on the filter with a sealing solution sandwiched therebetween so as to obtain a slide prepared for observation.

The slide thus obtained was observed with the use of a phase-contrast/fluorescence microscope (epifluorescence microscope BX-60, manufactured by Olympus Corporation). First, the slide was observed with the use of a phase-contrast microscope to confirm amosite fibers, and then an identical visual field was observed by switching a light path to a fluorescence mode.

FIG. 1 is a view showing a result of the asbestos microscopic observation using the phase-contrast fluorescence method. (A) of FIG. 1 shows a result of a case where "H-NS$_{60-90}$-Streptavidin-Cy3" is used as the fluorescent protein. (B) of FIG. 1 shows a result of a case where "H-NS$_{60-90}$-Streptavidin-DyLight488" is used as the fluorescent protein. (C) of FIG. 1 shows a result of a case where "H-NS$_{60-90}$-Streptavidin-DyLight550" is used as the fluorescent protein. (D) of FIG. 1 shows a result of a case where "H-NS$_{60-90}$-Streptavidin-CF555" is used as the fluorescent protein. (E) of FIG. 1 shows a result of a case where "H-NS$_{60-90}$-Streptavidin-CF488A" is used as the fluorescent protein. In (A) to (E) of FIG. 1, the left portion shows a phase-contrast microscope image, and the right portion shows a fluorescence microscope image in an identical visual field to the phase-contrast microscope image. As shown in FIG. 1, binding of the fluorescent protein to the amosite fiber observed under the phase-contrast microscope could be confirmed under the fluorescence microscope.

Note that a U-MNG cube (dichroic mirror: DM570, excitation filter: BP530-550, absorption filter: BA590) was used to observe the fluorescent pigments Cy3, DyLight550, and CF555, and a U-NIBA cube (dichroic mirror: DM505, excitation filter: BP470-490, absorption filter: BA515-550) was used to observe the fluorescent pigments DyLight488 and CF488A. A microscopic digital camera DP-70 (Olympus Corporation) was used to capture an image.

Note that a fluorescence intensity (=protein binding amount+fluorescent substance intensity) of a fiber before and after the transparentizing step was evaluated by measuring luminance. Specifically, luminance of a fiber in an image before and after the transparentizing step was measured with the use of image analysis software VH Analyzer (KEYENCE), and thus a ratio of maintenance of a fluorescence intensity was calculated. As a result, as for "H-NS$_{60-90}$-Streptavidin-Cy3", assuming that its fluorescence intensity before the transparentizing step is 100%, 90% was maintained after the transparentizing step. As for "H-NS$_{60-90}$-Streptavidin-DyLight488", assuming that its fluorescence intensity before the transparentizing step is 100%, 90% was maintained after the transparentizing step. As for "H-NS$_{60-90}$-Neutravidin-DyLight550", assuming that its fluorescence intensity before the transparentizing step is 100%, 80% was maintained after the transparentizing step. As for "H-NS$_{60-90}$-Streptavidin-CF555", assuming that its fluorescence intensity before the transparentizing step is 100%, 80% was maintained after the transparentizing step. As for "H-NS$_{60-90}$-Streptavidin-CF488A", assuming that its fluorescence intensity before the transparentizing step is 100%, 90% was maintained after the transparentizing step.

It was thus confirmed that amosite can be detected by the phase-contrast fluorescence method by using, as an asbestos-binding protein, the H-NS$_{60-90}$ protein and using, as a fluorescent label, Cy3, DyLight488, DyLight550, CF555, or CF488A.

Example 3

Microscopic Observation of Asbestos by Phase-Contrast Fluorescence Method (2)

A slide was prepared by the same method as that of Example 2 except for that (i) a membrane filter on which amosite (brown asbestos) (JAWE231) and rock wool (JFM standard fibrous sample) serving as test samples were collected was used and (ii) only "H-NS$_{60-90}$-Streptavidin-Cy3" was used for a fluorescently-labeled protein.

The slide thus obtained was observed with the use of a phase-contrast/fluorescence microscope (epifluorescence microscope BX-60, manufactured by Olympus Corporation). First, the slide was observed with the use of a phase-contrast microscope to confirm fibrous substances, and then an identical visual field was observed by switching a light path to a fluorescence mode.

Figure 2:
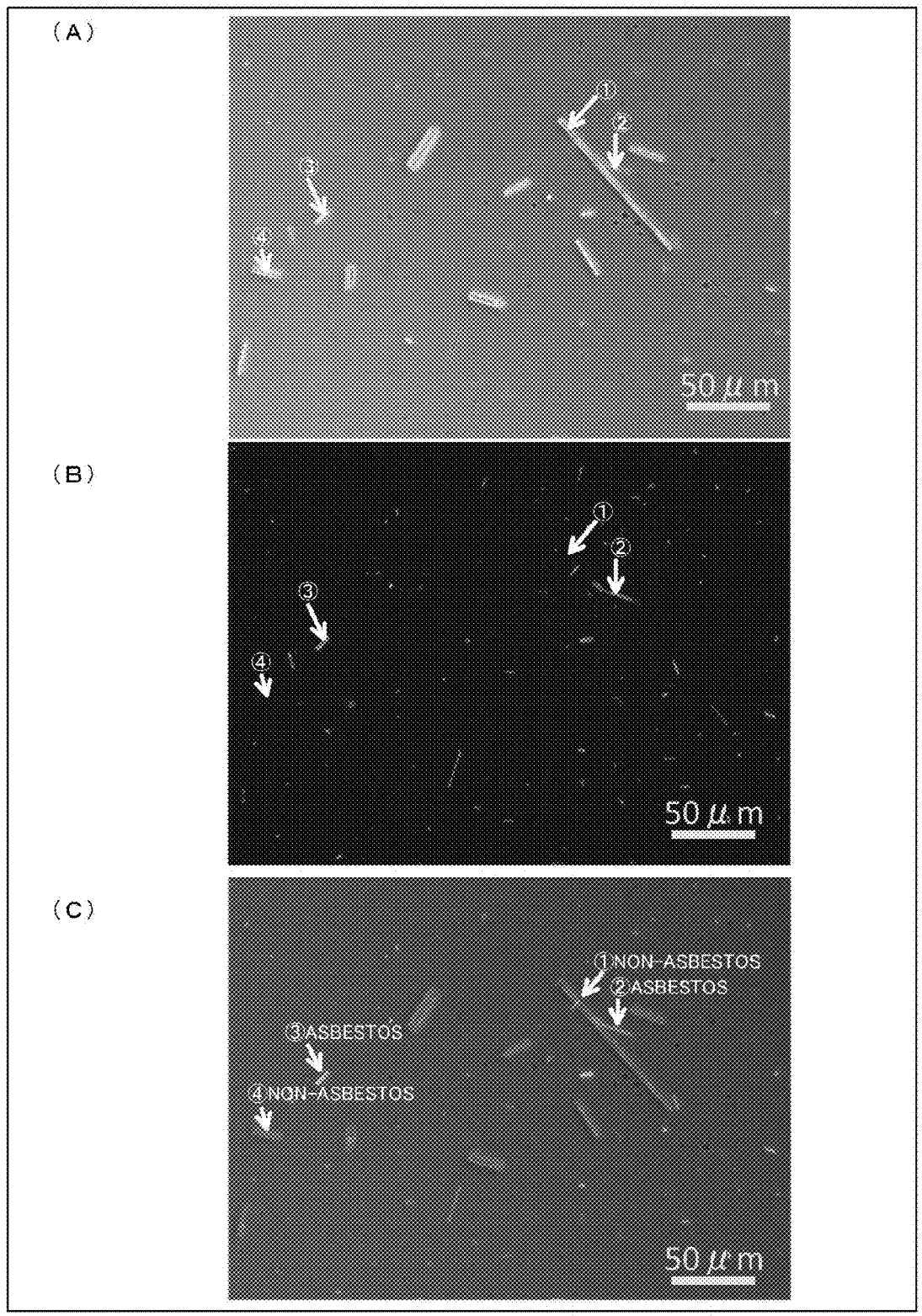
FIG. 2 is a view showing a result of asbestos microscopic observation using a phase-contrast fluorescence method.

FIG. 2 is a view showing a result of the asbestos microscopic observation using the phase-contrast fluorescence method. (A) of FIG. 2 shows a phase-contrast microscope image, (B) of FIG. 2 shows a fluorescence microscope image in an identical visual field to the phase-contrast microscope image of (A) of FIG. 2, and (C) of FIG. 2 shows an image obtained by superimposing the phase-contrast microscope image of (A) of FIG. 2 and the fluorescence microscope image of (B) of FIG. 2 on each other. As shown in FIG. 2, binding of the fluorescent protein to fibrous substances 2 and 3 observed under the phase-contrast microscope could be confirmed under the fluorescence microscope. Meanwhile, binding of the fluorescent protein to fibrous substances 1 and 4 observed under the phase-contrast microscope could not be confirmed under the fluorescence microscope. As a result, it was determined that the fibrous substances 2 and 3 were asbestos, and it was determined that the fibrous substances 1 and 4 were not asbestos.

It was thus confirmed that use of the phase-contrast fluorescence method makes it possible to highly efficiently, easily, and accurately determine whether a fibrous substance observed under a phase-contrast microscope is asbestos or not.

Example 4

Preparation of Asbestos-Binding Protein Dksa and Fluorescent Label

Next, PCR was carried out with the use of an oligonucleotide primer P5 (GGAATTCGCTAGCATGCAA-GAAGGGCAAAACCG: SEQ ID NO:5) and an oligonucleotide primer P6 (GTTGGATCCCCGCAGCCAGCCATCTGTTTTTCGC: SEQ ID NO:6) by using genome DNA of an *E. coli* K-12 strain (*Escherichia coli* K12, ATCC 700926) as a template to amplify a gene encoding a DksA protein (database name: GenBank, accession No.: AAC73256) which is an asbestos-binding protein. The PCR was carried out with the use of a KOD-plus DNA polymerase (TOYOBO) in accordance with TOYOBO's protocol.

A PCR amplification product thus produced and an protein expression vector ET21-b were treated with the use of restriction enzymes NheI and BamHI at 37° C. for 1 hour, and subjected to agarose gel electrophoresis. A DNA fragment in cut-out-gel of the agarose gel electrophoresis was ligated with the use of Ligation High (TOYOBO) at 16° C. for 30 minutes and transform the *E. coli* JM109 strain with the ligated. From a colony of the transformed *E. coli* JM109 strain, a plasmid into which a target DNA fragment was inserted was extracted. This plasmid was named "pET-DksA".

Rosetta™ (DE3) pLysS (Novagen) transformed with the use of pET-DksA was cultured overnight at 37° C. with the use of a 2×YT medium, and 1% (v/v) of a culture thus obtained was inoculated into a 200 ml LB medium [10 g/l tryptone, 5 g/l yeast extract, 5 g/l NaCl]. After culturing at 37° C. until $OD_{600}$ becomes 0.6, IPTG (isopropyl-(3-D-thioglactopyranoside) was added to a final concentration of 0.5 mM, and a mixture was cultured at 28° C. for 4 hours. Bacteria thus cultured were collected by centrifugation of a culture solution. To a bacteria pellet thus obtained, 10 ml of a buffer solution A [0.05M Tris-HCl (pH8.3), 0.05M NaCl, 10% glycerol] was added to suspend the bacteria, and the bacteria was crushed by ultrasonic waves.

A cell breakage solution thus obtained was supplied to a Histrap FF column, so as to adsorbed to the column a DksA protein having histidine at its C-terminus. Then, the DksA protein was eluted out from the column with the use of a buffer solution B [0.05M Tris-HCl (pH 8.3), 0.05M NaCl, 10% glycerol, 0.5M imidazole]. Polyacrylamide electrophoresis was performed with the DksA protein thus obtained. The polyacrylamide electrophoresis shows that a degree of purification of the DksA protein thus obtained is 95% or more.

Next, the DksA protein was fluorescently labeled. First, the DksA protein was labeled with fluorescein. Then, 5 nmol of the DksA protein was dissolved in 400 µl of a 25 mM HEPES-NaOH buffer solution (pH 7.4) containing 50 mM NaCl and 10% glycerol. After 4.3 µl of 10 mg/ml fluorescein-5-maleimido (Thermo Scientific)/dimethylformamide was added to the solution, the mixture was left at rest at a dark place at the room temperature for 2 hours. The reaction solution was purified by removing unbound fluorescein by gel filtration. This DksA labeled with fluorescein was named "DksA-Fluorescein".

Next, DksA was labeled with Alexa488. Then, 5 nmol of the DksA protein was dissolved in 400 µl of a 25 mM HEPES-NaOH buffer solution (pH 7.4) containing 50 mM NaCl and 10% glycerol. After 6.4 µl of 10 mg/ml Alexa488-5-maleimido (invitrogen)/dimethylformamide was added to the solution, the mixture was left at rest at a dark place at the room temperature for 2 hours. The reaction solution was purified by removing unbound Alexa488 by gel filtration. This DksA protein labeled with Alexa488 was named "DksA-Alexa488".

Example 5

Microscopic Observation of Asbestos by Phase-Contrast Fluorescence Method (3)

A slide was prepared by the same method as that of Example 2 except for that (i) a membrane filter on which chrysotile (white asbestos) (JAWE111) serving as a test sample was collected was used, (ii) DksA-Fluorescein (350 nM) or DksA-Alexa488 (200 nM) was used as a fluorescent protein, and (iii) a buffer solution D [0.1M carbonate buffer solution (pH 9.4), 1.0% Tween80 (Registered Trademark)] was used as a buffer solution.

The slide thus obtained was observed with the use of a phase-contrast/fluorescence microscope (epifluorescence microscope BX-60, manufactured by Olympus Corporation). First, the slide was observed with the use of a phase-contrast microscope to confirm chrysotile fibers, and then an identical visual field was observed by switching a light path to a fluorescence mode.

Figure 3:
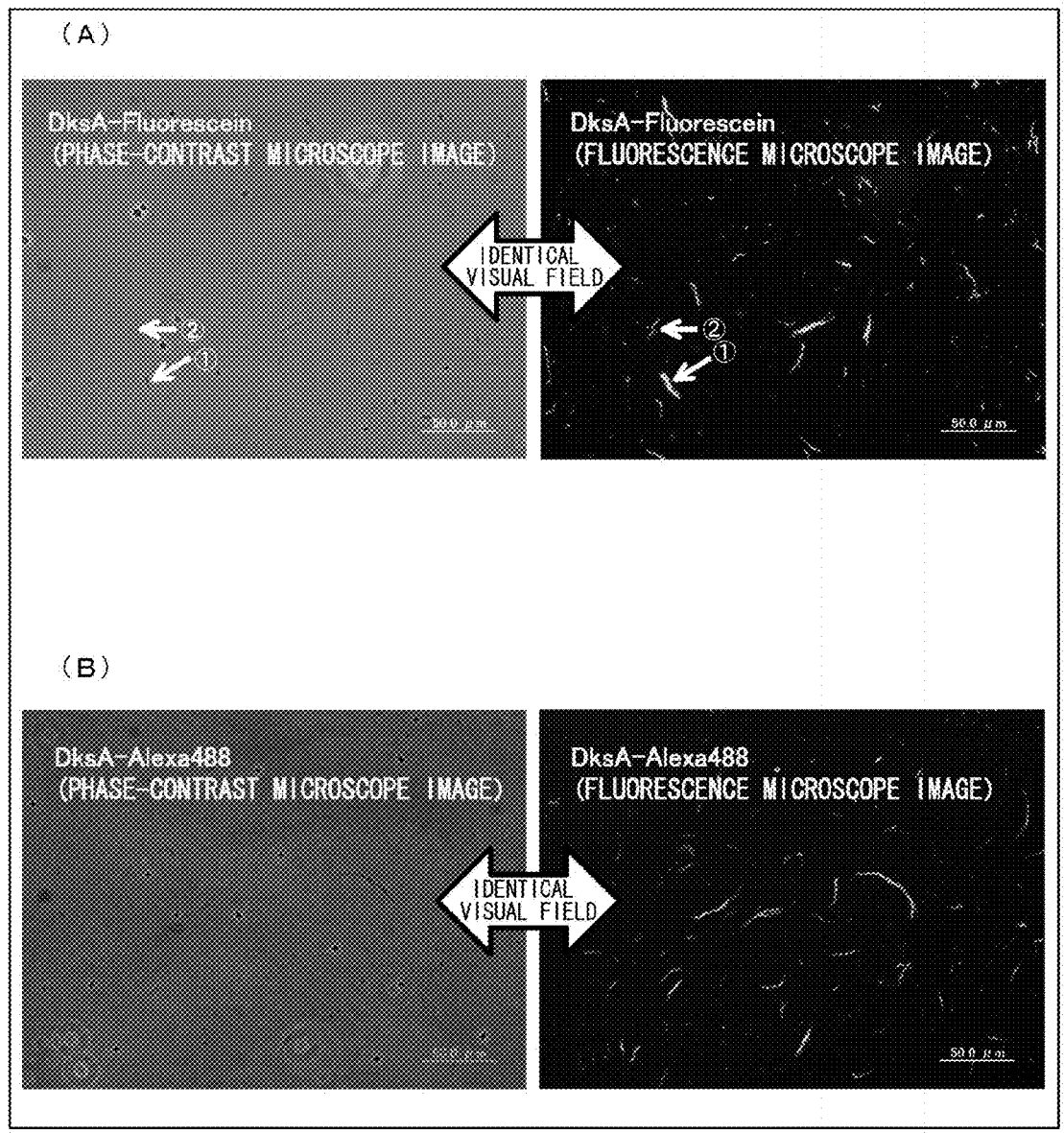
FIG. 3 is a view showing a result of asbestos microscopic observation using a phase-contrast fluorescence method.

FIG. 3 is a view showing a result of the asbestos microscopic observation using the phase-contrast fluorescence method. (A) of FIG. 3 shows a result of a case where "DksA-Fluorescein" is used as the fluorescent protein. (B) of FIG. 3 shows a result of a case where "DksA-Alexa488" is used as the fluorescent protein. In (A) and (B) of FIG. 3, the left portion shows a phase-contrast microscope image, and the right portion shows a fluorescence microscope image in an identical visual field to the phase-contrast microscope image. As shown in FIG. 3, binding of the fluorescent protein to the chrysotile fiber observed under the phase-contrast microscope could be confirmed under the fluorescence microscope.

As shown in (A) of FIG. 3, as for a substance 1, fibers can be confirmed under the phase-contrast microscope, and binding of the fluorescent protein to the fibers can be confirmed under the fluorescence microscope. Meanwhile, as shown in (A) of FIG. 3, as for a substance 2, binding of the fluorescent protein to fibers can be confirmed under the fluorescence microscope. However, since these fibers are fine fibers having a width (diameter) of less than 0.25 µm, these fibers are not generally detected as asbestos under the phase-contrast microscope. According to the phase-contrast fluorescence method, such fine asbestos fibers are excluded in the first detection step of detecting a predetermined fibrous substance under the phase-contrast microscope. This eliminates a risk that fibers, such as the substance 2, that are not detected as asbestos under the phase-contrast microscope are included in the total number of finally detected asbestos.

Note that a U-NIBA cube (dichroic mirror: DM505, excitation filter: BP470-490, absorption filter: BA515-550) was used to observe the fluorescent pigment fluorescein and the fluorescent pigment Alexa488. A microscopic digital camera DP-70 (manufactured by Olympus Corporation) was used to capture an image.

Note that a fluorescence intensity (=protein binding amount+fluorescent substance intensity) of a fiber before and after the transparentizing step was evaluated by a similar method to that used in Example 2. As a result, as for "DksA-Fluorescein", assuming that its fluorescence intensity before the transparentizing step is 100%, 80% was maintained after the transparentizing step. As for "DksA-Alexa488", assuming that its fluorescence intensity before the transparentizing step is 100%, 80% was maintained after the transparentizing step.

It was thus confirmed that chrysotile can be detected by the phase-contrast fluorescence method by using the DksA protein as, an asbestos-binding protein, and using fluorescein and Alexa488 as a fluorescent label.

INDUSTRIAL APPLICABILITY

As described above, according to the method of the present invention for detecting asbestos, it is possible to detect asbestos more efficiently, easily and accurately without changing the asbestos detection criterion according to the conventional method such as the phase-contrast microscope/electron microscope method, as compared with the phase-contrast microscope/electron microscope method. Therefore, the present invention is extremely important as means for coping with an asbestos risk at a demolition work site etc. which require speediness in asbestos detection.

Accordingly, the present invention is applicable to various kinds of industries such as industries handling asbestos and industries detecting asbestos.

The invention claimed is:

1. A method for detecting asbestos, comprising the steps of:
   a) contacting an asbestos-binding protein complex having a fluorescent label with a test substance;
   b) detecting a fibrous substance contained in the test substance with use of a phase-contrast/fluorescence microscope in phase-contrast mode, the fibrous substance having a length of 5 μm or more, a width of less than 3 μm, and a length-width ratio of 3:1 or more; and
   c) determining that the fibrous substance to which the asbestos-binding protein complex is bound is asbestos by detecting, with use of the phase-contrast/fluorescence microscope in fluorescence mode, the asbestos-binding protein complex bound to the fibrous substance detected in step b) based on the fluorescent label; and
   wherein step b) and step c) are carried out without changing a visual field of the phase-contrast/fluorescence microscope, and
   wherein the asbestos-binding protein complex comprises four biotin-modified H-NS$_{60-90}$ asbestos binding polypeptides and a fluorescently-labeled streptavidin, wherein each of the biotin-modified asbestos binding polypeptides has an amino acid sequence consisting of SEQ ID NO:8 and one biotin molecule at the C-terminus and wherein the biotin-modified asbestos polypeptides bind to the fluorescently-labeled streptavidin through a biotin-streptavidin interaction.

2. The method according to claim 1, wherein:
   the test substance is collected with use of a filter;
   the contact between the asbestos-binding protein complex having a fluorescent label and the test substance in step a) occurs on the filter;
   the method further comprises a transparency step of making the filter transparent by spraying an acetone vapor on the filter after the contacting step a); and wherein
   step b) is carried out after the transparency step.

3. The method according to claim 1, wherein steps b) and c) are repeated at least one time.

4. The method according to claim 2, wherein:
   the asbestos-binding protein complex binding with the fibrous substance is maintained after the transparency step; and
   the fluorescent label is one whose fluorescence can be detected by the phase-contrast/fluorescence microscope in fluorescence mode after the transparency step.

5. The method according to claim 4, wherein the fluorescent label is at least one fluorescent substance selected from the group consisting of Cy3, DyLight488, fluorescein, Alexa488, ATTO488, CF488A, DyLight550 and CF555.

* * * * *